United States Patent
Spall et al.

(10) Patent No.: US 8,242,062 B2
(45) Date of Patent: Aug. 14, 2012

(54) IMS DETECTION OF CHEMICAL MARKERS IN PETROLEUM PRODUCTS

(75) Inventors: W. Dale Spall, Los Alamos, NM (US); Karen Mehlin, Los Alamos, NM (US); Gary Elceman, Las Cruces, NM (US); Hartwig Schmidt, Las Cruces, NM (US)

(73) Assignee: Authentix, Inc., Addison, TX (US)

( * ) Notice: Subject to any disclaimer, the term of this patent is extended or adjusted under 35 U.S.C. 154(b) by 552 days.

(21) Appl. No.: 11/695,564

(22) Filed: Apr. 2, 2007

(65) Prior Publication Data

US 2007/0212785 A1 Sep. 13, 2007

Related U.S. Application Data

(63) Continuation of application No. 10/354,243, filed on Jan. 29, 2003, now Pat. No. 7,208,451.

(51) Int. Cl.
*C10M 129/00* (2006.01)
*C10L 1/18* (2006.01)
*G01N 33/22* (2006.01)
*G01N 33/26* (2006.01)

(52) U.S. Cl. ......... 508/110; 508/577; 508/578; 44/300; 44/437; 436/27; 436/29; 436/56

(58) Field of Classification Search ............... 436/56; 44/300; 508/110
See application file for complete search history.

(56) References Cited

U.S. PATENT DOCUMENTS

| | | | |
|---|---|---|---|
| 4,018,693 A | 4/1977 | Mead et al. | |
| 4,209,302 A | 6/1980 | Orelup | |
| 5,525,516 A | 6/1996 | Krutak et al. | |
| 5,672,182 A | 9/1997 | Smith | |
| 5,843,783 A | 12/1998 | Rutledge et al. | |
| 5,928,954 A * | 7/1999 | Rutledge et al. | 436/56 |
| 5,962,330 A | 10/1999 | Frederico et al. | |
| 5,984,983 A | 11/1999 | Asgaonkar et al. | |
| 6,274,381 B1 | 8/2001 | Pauls et al. | |
| 6,312,958 B1 * | 11/2001 | Meyer et al. | 436/56 |
| 6,482,651 B1 | 11/2002 | Smith et al. | |
| 6,514,917 B1 | 2/2003 | Smith et al. | |

(Continued)

FOREIGN PATENT DOCUMENTS

WO  WO 97/41092  11/1997

OTHER PUBLICATIONS

European Office Action, Application No. 04 706 455.5, dated Nov. 5, 2007.

*Primary Examiner* — Ellen McAvoy
(74) *Attorney, Agent, or Firm* — Kelly Kordzik; Matheson Keys Garsson & Kordzik PLLC

(57) ABSTRACT

A method and composition for identifying chemically tagged petroleum products can be achieved by adding one or more chemicals to a selected petroleum product wherein the chemical is immune to extraction from the petroleum product by conventional inexpensive absorbents, cannot be removed by extraction with acids, bases, or immiscible solvents, cannot be easily oxidized, reduced or reacted with common agents, is difficult to disguise by masking with other agents, has a low polarity, and has a boiling point in the range of the petroleum products the chemical is being added to. The presence of the chemical is determined by using ion mobility spectroscopy.

26 Claims, 1 Drawing Sheet

U.S. PATENT DOCUMENTS

Figure 1:
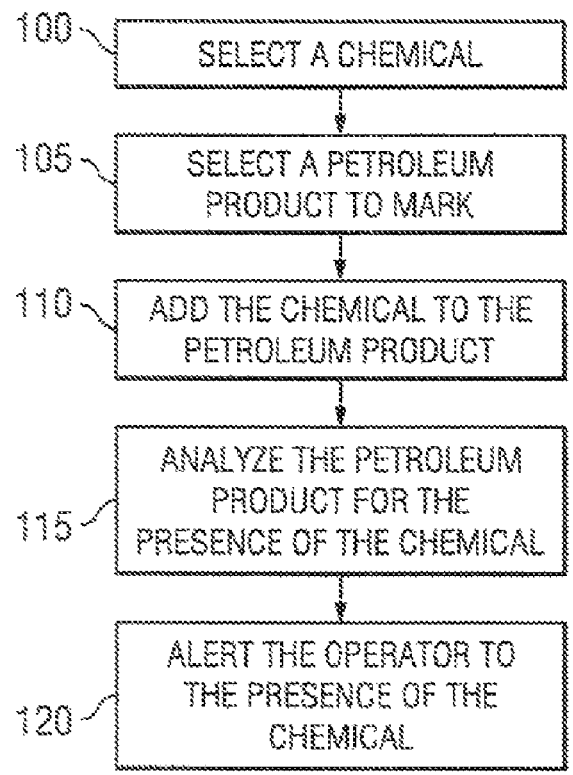

| | | | |
|---|---|---|---|
| 6,794,645 B2 * | 9/2004 | Kanik et al. | 250/288 |
| 6,808,542 B2 * | 10/2004 | Nguyen et al. | 44/300 |
| 7,208,451 B2 * | 4/2007 | Spall et al. | 508/110 |
| 2002/0173042 A1 * | 11/2002 | Oolman et al. | 436/56 |
| 2004/0102340 A1 * | 5/2004 | Ho et al. | 508/550 |
| 2004/0147413 A1 | 7/2004 | Spall et al. | |
| 2005/0019939 A1 * | 1/2005 | Spall et al. | 436/139 |
| 2006/0228802 A1 * | 10/2006 | Tiller et al. | 436/56 |

* cited by examiner

IMS DETECTION OF CHEMICAL MARKERS IN PETROLEUM PRODUCTS

PRIORITY BENEFIT

This patent application is a continuation of U.S. patent application Ser. No. 10/354,243, filed Jan. 29, 2003.

FIELD OF THE INVENTION

This invention relates to a method and apparatus for using ion mobility spectroscopy to monitor specific classes of compounds in petroleum products.

BACKGROUND OF THE INVENTION

The problem of tax evasion by passing custody markers is a major problem in many countries. In the U.S.A., a colored dye is added to diesel to visually identify the fuel for tax-exempt use in off-road situations. The colored diesel is exempt from federal taxes, principally because the main purpose of the tax is for the funds to be used in highway development and maintenance. However, the coloring agent may be removed by relatively simple methods such as acid/base reactions. The coloring agent is often removed because it is profitable to remove the coloring agent and use the tax-exempt fuel in on-road vehicles.

What is needed is a chemical that can be co-added with the colored dye, and provides a more secure technique for the field determination of the presence of the dyed product. The chemical should not be easily removed using simple methods. Also, it would be beneficial if no sample preparation of the compound is required, little training of the monitoring personnel is required, and the chemicals used for marking or tagging the fuel were relatively inexpensive and could be used either singly or in combinations to provide a number of distinctly different marker sets.

SUMMARY

The invention provides a chemical marker and a method for identifying chemical markers in petroleum products using ion mobility spectroscopy (IMS). The chemical markers have a relatively low solubility in polar solvents and are non-reactive with acids and bases. The markers consist of chemicals that can be co-added with the colored dye, cannot be removed using simple methods, and provide a more secure technique for the field determination of the presence of the dyed product. The chemicals can be used either singularly or in combinations to provide a number of distinctly different marker sets. In addition, no sample preparation is required, and little training of the monitoring personnel is needed. The analytical technique for field determination of the presence of these chemicals is determined by using a laboratory based or hand held IMS.

IMS, sometimes also called plasma chromatography, is a technique that separates ions on the rate of their movement in an electric field. The technique is similar to time of flight mass spectroscopy, except that IMS does not involve the use of a high vacuum but operates at near atmospheric pressure. IMS units are becoming widely used as chemical detectors for explosives, chemical agents, and as monitors of hazardous substances in the atmosphere. The development since their introduction over a decade ago has been steady. Improvement in ion generation, detection, and data interpretation are becoming more sophisticated and precise over time. Current units are relatively inexpensive and reasonably small.

Functionally, a sample is typically introduced as a vapor to the IMS. The primary method of introduction is to "sniff" or draw in the atmosphere above the sample, typically called a headspace, by using a pump contained within the IMS. The pressure of the headspace is typically between 0-2 Atmospheres. The vapors in the headspace are drawn into a chamber by the pump. Once the vapors are in the chamber, they are ionized by a gentle ionization source, the most common being nickel 63, a radioactive source that ionizes the vapor by the emission of low energy beta particles. Recently, corona discharge sources have been introduced. Corona discharge sources are preferred for general use since there are fewer hazards associated with then than with the radioactive nickel source. Both sources are based on the ionization principal.

After ionization, the ions enter a region defined by an electric potential gradient end into a drift area. The drift area is nothing more than a region of space that has an electrostatic charge across it. The ions move down through the drift area until they hit a detector. The ions from the different species present travel through the drift area at distinct characteristic speeds. The difference in arrival time of the ions at the detector is a means for identifying each of the different types of molecules in the initial mixture. The use of IMS units is known in the art. One example of a handheld IMS that could be used in accordance with the present invention is the Sabre 2000 by Smiths Detection. One example of a laboratory IMS that could be used in accordance with the present invention is the Ionscan 400B by Smiths Detection of Edgewood, Md.

DETAILED DESCRIPTION OF THE DRAWINGS

Figure 2:
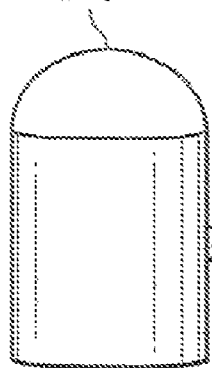
Figure 2:
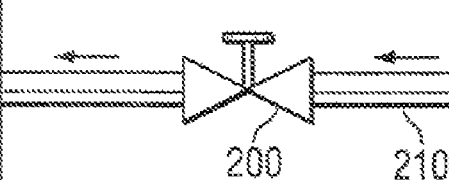

A better understanding of the invention can be obtained from the following detailed description of one exemplary embodiment as considered in conjunction with the following drawings in which:

FIG. 1 is a block diagram depicting the steps of identifying a chemically tagged petroleum product; and FIG. 2 is a block diagram depicting a pipe line for a petroleum product including a method.

DETAILED DESCRIPTION OF EXEMPLARY EMBODIMENTS

In the descriptions that follow, like parts are marked throughout the specification and drawings with the same numerals, respectively. The drawing figures are not necessarily drawn to scale and certain figures may be shown in exaggerated or generalized form in the interest of clarity and conciseness.

Although the method described below specifically addresses the identification of tax evasion is diesel fuels, the general technique is applicable to a wide range of petroleum products and can determine authenticity of these products in a range of circumstances. Petroleum products include, but are not limited to, fuels, oils, and lubricants.

As shown in FIG. 1, step 100, the first step is to select a chemical to be used in marking or tagging a selected petroleum product, step 105. The terms marking and tagging are used interchangeably. Once the chemical has been selected, it is added to the petroleum product and mixed until the chemical is uniform throughout the petroleum product, step 110. Next, at some later time, the petroleum product may be analyzed with a hand held IMS device or some other similar device used for detection of the added chemical, step 115. If the added chemical is present, the IMS will alert to operator to the presence of the chemical, step 120. After the IMS has signaled the presence, or non-presence, of the added chemical, the user is free to select the next course of action. For example, if the chemical is present in a petroleum product that is improperly labeled "taxed" when the product should be labeled a "tax" free product, the user may quarantine the petroleum product, issue a citation, or take a sample of the petroleum product to a laboratory for further testing.

When selecting the chemical to be used, the chemical must be immune to extracting from the petroleum product by most normal means. By normal means, it is meant that the chemical cannot be differentially absorbed from the product using conventional inexpensive absorbents, cannot be removed by extraction with acids, bases, or immiscible solvents, cannot be easily oxidized, reduced or reacted with common agents to effectively remove them, and the chemical should be difficult to disguise by masking with other agents. In addition, the chemical should have a low polarity as well as a boiling point in the range of the petroleum product the chemical is being used so the chemical is easily detected by the IMS. Also, because the IMS uses a low energy excitation for the ions, the chemical should have an electronegative group that is easily ionizable.

Preferably, the chemical's boiling point should be in the range of 85° Centigrade (C)–750° C. The boiling point range is based on the chemicals being hidden in the boiling fractions of the specific petroleum product. For example, in diesel fuel, the large mass fraction comes off in the boiling range of 200°-250° C. Chemicals with boiling points around that range essentially have the same vapor pressure as the diesel fuel resulting in a reasonable amount of chemical concentration in the headspace. Therefore, when you sniff the headspace with an IMS, the chemical will be easily detected. If the boiling point is too high, there may not be enough of the chemical present in the headspace to detect, creating detection problems. If the boiling point is too low the chemical may evaporate too readily creating saturation problems with the detection device.

Many organic molecules containing C, H, N, O, S and P, have the above required characteristics and are relatively inexpensive. The specific classes of chemicals available for use as a chemical to tag petroleum products all have the general formula:

RCAR'

The R and R' group can be the same or they can be different. Examples of the R group include alkyl, olefin, aryl, heterocycle or hydrogen. The A group can be a ketone, alcohol, amines including low alkeyal amines, cyano, sulfate, nitrile, nitrate, halogen, organic acid group, mercaptan compounds, aldehyde, formyl, thiocyano and isothiocyano. All of the above listed compounds are commercially available and known in the art. Selection of chemicals is based on what the IMS is set to detect and the cost of the chemical.

By way of illustration and not as a limitation, the following specific compounds may be used, 2-Octanone, 3-Octanone, 3,5-dimethyl-4-octanone, 3-methyl-4-octanone, 4-octanone, 5-hydroxy-4-octanone, 5-nitro-2-octanone, 2,6-dimethyl-3-heptanone, 2,6-Dimethyl-4-heptanone, 2-Heptanone, 2-methyl-4-heptanone, 2-Methyl-3-heptanone, 3-Heptanone, 4-Heptanone, 2-Nonanone, 3-Nonanone, 4-Nonanone, 5-Nonanone, 3-methyl-4-nonanone, 2,8-dimethyl-5-nonanone, 7-ethyl-2-methyl-4-nonanone, 2-Decanone, 2-methyl-3-decanone, 3-Decanone, 4-Decanone, 4-methyl-5-decanone, 2,2-dimethyl-3-undecanone, 2-methyl-3-undecanone, 2-methyl-4-undecanone, 2-Undecanone, 6-Undecanone, 7-ethyl-2-methyl-4-undecanone, 2-dodecanone, 3-dodecanone, 5-dodecanone, 2-Tridecanone, 3-Tridecanone, 7-Tridecanone, 3-Tetradecanone, 2-Pentadecanone, 4-Pentadecanone, 5-Pentadecanone, 6-Pentadecanone, 7-Pentadecanone, Pentadecanone, 8-Pentadecanone, 2,6-dimethyl-10-hexadecanone, 2-Hexadecanone, 3-Hexadecanone, 7-Hexadecanone, 2-Hexadecanone, 4-Heptadecanone, 6-Heptadecanone, 7-Heptadecanone, 8-Heptadecanone, 2-Octadecanone, 3-Octadecanone, 5-Octadecanone, 9-Octadecanone, 2-nonadecanone, 9-nonadecanone, 1,2,3-Triphenyl benzene, 1,3,4-Triphenyl benzene, 1-Acetylnaphthalene, 2-Acetonaohthone, Thiophene, 2-Acetylthiophene, 3-Acetylthiophene, Propiophenone, 2,2-Dimethyl-propiophenone, 2,4'-Dimethyl-propiophenone, 3'-(cyanomethyl)-2,2-Dimethyl-propiophenone, 4'-(cyanomethyl)-2,2-Dimethyl-propiophenone, 3-phenyl-3-(phenylthio) propiophenone, 4,4'-methylenebis (propiophenone), 1-Phenyl-2-butanone, 3-phenyl-2-butanone, 4-Phenyl-2-butanone, 3,3-Dimethyl-2-butanone, 1,1,5,5-tetraphenyl-3-pentanone, 1,1-diphenyl-3-pentanone, 1-phenyl-2-pentanone, 1-phenyl-3-pentanone, 2,2,4,4-Tetramethyl-3-pentanone, 2,2,4,4-Tetramethyl-3-pentanone imine, 2,2,4,4-Tetramethyl-3-pentanone, oxime, 2,4-Dimethyl-3-pentanone, 2-Methyl-3-pentanone, 2-phenyl-3-pentanone, N-butyl-tert-butyl-amine, (1-phenyl-ethyl)-p-tolyl-amine, dimethyl-(1-methyl-heptyl)-amine, dimethyl-(1-methyl-2-phenyl-propyl)-amine, 3-Pyridine-carbonitrile, 4-Pyridine-carbonitrile, Aniline, p-Propyl amisole, 2-ethyl-6-isopropylaniline, N-Ethyl-N-isopropyl/amines, BIS-(2,6-dimethyl-phenyl)-amine, dimethyl-(4-pyridin-4-YL-phenyl)-amine, Propylamine, (R)-(+)-β-Methylphenethylamine, (S)-(–)-β-Methylphenethylamine, 1-Dimethylamino-2-propylamine, 1-methyl-1-phenyl-propylamine, 2-Ethyl-1-hexylamine, 2-Amino-6-methylheptane, 2-Aminoheptane, Heptylamine, N,N-Diethyl-tert-octylamine, tert-butyl-tert-octylamine, tert-Amyl-tert-octylamine, tert-Octylamine, Octylamine, Nonylamine, Decylamine, Hexanenitrile, Heptanenitrile, Octanenitrile, Nonanenitrile, 2,4,6-Trimethylbenzyl cyanide, 2-aminophenyl-acetonitrile, 2-Methoxyphenyl-acetonitrile, 3,5-dimethoxy-benzyl cyanide, 3-Methoxyphenyl-acetonitrile, 4-Aminobenzyl cyanide, 4-Methoxyphenyl-acetonitrile, p-Tolyacetonitrile, 1-cyano-2-(3-methylphenyl)ethyl thiocyanate, 1-cyano-2-(3-nitrophenyl)ethyl thiocyanate, 1-cyano-2-(4-methylphenyl)ethyl thiocyanate, 2-((4-nitrophenyl)sulfonyl-1-phenylethyl thiocyanate, 2-naphthoylmethyl thiocyanate, 3,4-dimethoxyphenyl thiocyanate, 2-oxo-2-(2-thienyl)ethyl thiocyanate, 3-methylbenzyl thiocyanate, 3-nitro-1-azulenyl thiocyanate, 4'-(tetradecyloxy)phenacyl thiocyanate, 4-(dimethylamino) phenyl thiocyanate, 4-(hexadecyloxy)benzoylmethyl thiocyanate, 4-(n-benzyl-n-ethylamino)phenyl thiocyanate, 4-(n-benzyl-n-methylamino)phenyl thiocyanate, 4-acetamido-3-methoxyphenyl thiocyanate, 4-amino-2-nitrophenyl thiocyanate, 4-amino-3-nitrophenyl thiocyanate, 4-hydroxy-m-tolyl thiocyanate, 4-methyl-6-phenyl-2-pyrimidinyl thiocyanate, 4-nitrobenzyl thiocyanate, Benzyl thiocyanate, decyl thiocyanate, dodecyl thiocyanate, ethyl thiocyanate, mesityl thiocyanate, phenacyl thiocyanate, piperidine thiocyanate, triphenylmethyl thiocyanate, Tetrabutylammonium thiocyanate, 1-Adamantyl isothiocyanate, 1-Naphthyl isothiocyanate, 2,3,4,6-Tetra-O-acetyl-□-D-glucopyranosyl isothiocyanate, 2,4,6-trimethylphenyl isothiocyanate, 2,4-Dimethoxyphenyl isothiocyanate, 2,4-xylyl isothiocyanate, 2,5-Dimethoxyphenyl isothiocyanate, 2,6-Dimethylphenyl isothiocyanate, 2-Ethylphenyl isothiocyanate, 2-naphthyl isothiocyanate, 2-Phenylethyl isothiocyanate, 2-Piperidinoethyl isothiocyanate, 3,3,5-trimethylcyclohexyl isothiocyanate, 3,4,5-Trimethoxyphenyl isothiocyanate, 3-(Methylthio) phenyl isothiocyanate, 3-(Methylthio)propyl isothiocyanate, 3-methoxypropyl isothiocyanate, 3-Methoxyphenyl isothiocyanate, 3-Nitrophenyl isothiocyanate, 3-Pyridyl isothiocyanate, 4-(4-Isothiocyanatophenylazo)-N,N-dimethylaniline, 4-biphenylyl isothiocyanate, 4-Cyanophenyl isothiocyanate, 4-Dimethylamino-1-naphthyl isothiocyanate, 4-Ethylphenyl isothiocyanate, 4-isopropylphenyl isothiocyanate, 4-Methoxyphenyl isothiocyanate, 4-Methyl-2-nitrophenyl isothiocyanate, Olefin isothiocyanate, Benzoyl isothiocyanate, Benzyl isothiocyanate, Butyl isothiocyanate, Cyclohexyl isothiocyanate, Fluorescein isothiocyanate isomer I, Hexyl isothiocyanate, Phenyl isothiocyanate, o-Tolyl isothiocyanate, p-Tolyl isothiocyanate. All of the above compounds are commercially available.

In the preferred embodiment, the A group may be a ketone and the R group an alkyl. The preferred mechanism for the ketones are asymmetric ketones, with the R group being at least 3-4 carbons long and boiling points between 100° and 250° C. The boiling range of 100°-250° C. is sufficiently similar to the boiling range of diesel fuel, 200°-250° C., to produce a reasonable concentration of the chemical in the head space.

It is preferable to have the ketone function away from the end of the molecule and near the middle. If the ketone function is not near the middle of the molecule, the molecule is relatively polar and could easily be extracted. If the ketone is in the middle of the compound, the dipole of the compound is lower and it is not as likely to be extracted by polar solvents.

While any chain length, or even no chain length, can be used, the preferred range on most of the compounds is from C6-C16. The chain length of the compound will change somewhat to keep the dipole as low as possible to avoid extraction by polar solvents. For example, sulfates have a higher dipole, so the chain length should be smaller.

After the chemical has been selected it is added to the petroleum product. The petroleum product may be contained in a transport container such as a tanker truck, tanker ship, pipeline 210 (FIG. 2), or any other process known in the art for transporting petroleum products from one point to another. For example and not by way of limitation, if the petroleum product is in a pipe line 210, the chemical may be injected into the petroleum stream through injection valve 200, as the petroleum product flows from processing plant 205 to storage container 215. If the petroleum product is in a tanker truck or ship, the chemical may be added by opening a port to the transport container and adding the chemical directly through the port. Also, the chemical could be injected into the transport container below the fuel level. The petroleum product may also be in a static storage container either above ground or below ground. If the petroleum product is in static storage container, the chemical may be added to opening a port to the static container and adding the chemical directly through the port or the chemical could be injected into the container below the fuel level. The petroleum product may also be added to a dry container before the petroleum product is added.

In the case of diesel fuel, it may be preferable to add the selected chemical at the same time the coloring dye is added at the taxation terminal. No particular solvent is necessary as most of the above listed chemicals are already in a liquid form. If the chemical is in liquid form, it is either directly added to the diesel fuel or diluted and then an added to the diesel fuel. The diesel fuel is typically in a tanker truck and the natural transport of the diesel fuel in tanker truck will properly mix the added chemical. However, if the diesel fuel is in a stationary tank, then some sort of physical mixing such as Vaughan's Rotamix system or some other mixing process known in the art may have to be performed into order to achieve a uniform mixture of the diesel fuel and added chemical.

If the chemical to be added is or might become a solid, it should be mixed with a solvent. The solvent should be non-reactive and totally miscible with the petroleum product. If a solvent is to be used, it is preferable the solvent is the petroleum product itself. For example, to mix a ketone with diesel fuel, the diesel fuel could be the solvent.

In some instances a solid material may be preferred. For example, it may be desirable for the chemicals to be time released. The chemical could be introduced in a solid form, encased in latex spheres, in hollow porous spheres, encased in a solid material that is soluble in the petroleum product, or some other similar type method. How the chemical is introduced to the petroleum product is based on the form of material that was added. For example, if the chemical was added in a solid form, the chemical would dissolve into the petroleum product. If the chemical is encased in a latex sphere, the sphere shell may be added as a dispersion that would dissolve in the petroleum product and release the chemical once the shell has dissolved. If the solid material is porous, then the chemical could leak out at a desired rate. An example of a porous hollow sphere would be a hollow metal sphere with pore sizes sufficient to allow the chemical inside to leak out or escape. The rate of escape would be dependent on the number and size of the pores. The type of solid material may depend on the available resources, type of chemical used or desired method of introduction for the solid or chemical.

The amount of chemical to be added is based on the desired concentration of the chemical in the headspace and the detection limits of the IMS. Preferably, the chemical is added is such an amount so the concentration of the chemical in the petroleum product is 1 ppb-100 ppm. In reality, the upper range is almost unlimited but is preferred to be 100 ppm or less due to cost of the chemical. If the concentration in the petroleum product is between 1 ppb-100 ppm, then the concentration of the chemical in the headspace should be about 100 ppb-1 ppm depending on the type of chemical used. Notably, the chemicals do not settle out and they do not separate and therefore, the concentration remains reasonably constant.

Testing for the presence of the chemical could be done in the field or in laboratory. If testing is to be done in a laboratory, then a sample of the petroleum product is taken and delivered to a laboratory that has the necessary equipment to analysis the petroleum product sample. Such necessary equipment is known in the art. One example of a laboratory IMS that could be used in accordance with the present invention is the Ionscan 400B by Smiths Detection. The laboratory could be in building or on a mobile unit such a truck or some other type of mobile laboratory known in the art.

Field determination for the presence of the added chemical includes opening the storage container, placing a handheld IMS device tuned to respond to the presence of the added chemical near the opening, and waiting a few seconds for the analysis to complete. Indication of the presence of the chemical would come from audible or visual alarm, and would signal for the operator to take appropriate action, such as sending the sample to a lab for a definitive analysis.

The IMS has the capability of detecting the relative concentrations of multiple species. Therefore, more than one chemical may be added to increase the marker set. For example two different C-9 ketones and a C-9 nitrile could be used. All three are separable and the relative ratio of the concentration could form a unique marker. Also, the added chemical could be a part of a larger marker set and used in conjunction with molecular markers such as those discussed in U.S. Pat. No. 5,525,516 whose disclosure is incorporated herein by reference. The use of molecular markers is known in the art.

The invention will now be illustrated with reference to the following specific, non-limiting examples.

Example One 4-heptanone is selected as the tagging chemical for use with diesel fuel in an 8,500-gallon tanker truck. 4-heptanone is an alkyl ketone with the double bonded oxygen in the $4^{th}$ carbon. The ketone, or A group, is in the middle of the compound thus making the dipole of the compound lower and therefore not as likely to be extracted by polar solvents. The boiling point for 4-heptanone is 145° C. and is within the desired range of 100°-250° C. for keytones. Approximately 10 gallons if diesel fuel is withdrawn from the tanker truck and mixed with 8.19 gallons of undiluted 4-heptanone. The resulting mixture is delivered back into the tanker truck to produce an overall concentration of 1 ppm-4-heptanone in the diesel fuel, assuming the density of the diesel fuel is 7.079 lb/gal, and the density of 4-heptanone is 6.8225 lb/gal. The concentration of 4-heptanone is within the desired concentration range of 1 ppb-100 ppm. The natural transporting of the diesel fuel thoroughly mixes the 4-heptanone with the diesel fuel. Upon arrival at the final destination of the diesel fuel, a handheld IMS designed specifically for the detection of ketones is able to detect the presence of 4-heptanone in the diesel fuel.

Example Two 6-undecanone was selected as the tagging chemical for use with diesel fuel in a 150,000-gallon above ground storage tank. 6-undecanone is an alkyl ketone with the double bonded oxygen on the $6^{th}$ carbon. The ketone, or A group, is in the middle of the compound thus making the dipole of the compound lower and therefore not as likely to be extracted by polar solvents. The boiling point for 6-undecanone is 191° C. and is within the desired range of 100°-250° C. for ketones. Approximately 10 gallons of diesel fuel was withdrawn from the storage tank and mixed with 147 gallons of undiluted 6-undecanone. The resulting mixture is delivered back into the storage tank to produce an overall concentration of 1 ppm 6-undecanone in the diesel fuel which is within the desired concentration range of 1 ppb-100 ppm, assuming the density of the diesel fuel is 7.079 lb/gal and the density of 6-undecanone is 6.9394. The 6-undecanone and diesel fuel thoroughly mixed using Vaughan's Rotamix system. At a later time, a handheld IMS designed specifically for the detection of ketones will be able to detect the presence of 6-undecanone in the diesel fuel.

Example 3

Methylphenylethyl amine is selected as the tagging chemical for use with jet fuel in an 8,500-gallon tanker truck. Methylphenylethyl amine has a relatively low dipole and is not as likely to be extracted by polar solvents. The boiling point for methylphenylethyl amine is 197-207° C. and is around the desired range of 200°-250° C. Approximately 9.469 gallons of methylphenylethyl amine is added directly into the tanker truck to produce an overall concentration of 1 ppm Methylphenyethyl amine which is within the desired concentration range of 1 ppb-100 ppm. The natural transporting of the jet fuel thoroughly mixed the methylphenethyl amine with the jet fuel. Upon arrival at the final destination of the jet fuel, a handheld IMS designed specifically for the detection of amines will able to detect the presence of methylphenylethyl amine in the jet fuel.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A method of determining the authenticity in a petroleum product comprising:
   (a) selecting a petroleum product;
   (b) analyzing the petroleum product using an ion mobility spectroscopy technique to determine whether the petroleum product comprises a chemical marker, wherein
     (i) the chemical marker has the general formula RCAR',
     (ii) the R component is selected from the group consisting of alkyl, olefin, aryl, and heterocycle groups and hydrogen,
     (iii) the R' component is selected from the group consisting of alkyl, olefin, aryl, and heterocycle groups and hydrogen,
     (iv) the A component is selected from the group consisting of ketones, alcohol, amines, cyano, sulfate, nitrile, nitrate, halogen, organic acid, mercaptan, aldehyde, formyl, thiocyano, and isothiocyano, and
     (v) the boiling point range of the chemical marker is within the boiling point range of the petroleum product; and
   (c) authenticating the petroleum product by the presence of the chemical marker.

2. The method of claim 1, wherein
   (i) the R component selected front the group consisting of aryl and heterocycle,
   (ii) R' is a compound selected from the group consisting of aryl and heterocycle groups.

3. The method of claim 2, wherein the concentration of the chemical marker in the petroleum product is between 1 ppb and 100 ppm.

4. The method of claim 2, wherein the concentration of the chemical marker in the petroleum product is between 100 ppb and 1 ppm.

5. The method of claim 2, wherein the step of analyzing is performed in a laboratory.

6. The method of claim 2, wherein the step of analyzing is performed by a field determination.

7. The method of claim 6, where in the step of authentication comprises sending a sample of the petroleum product to a laboratory for further analysis.

8. The method of claim 2, wherein the step of analyzing is performed using a hand-held device.

9. The method of claim 2, wherein the step of authenticating comprises a device that responds to the presence of the chemical marker by an audible or visual alarm.

10. The method of claim 1, wherein the step of analyzing the petroleum product comprises using the ion mobility spectroscopy technique to determine whether the petroleum product comprises a second chemical marker, wherein
   (a) the second chemical marker has the general formula RCAR';
   (b) the second chemical marker is different that the chemical marker;
   (c) further authenticating the petroleum product by the presence of the second chemical marker.

11. The method of claim 1, further comprising
(a) analyzing the petroleum product using an infrared detection technique to determine whether the petroleum product comprises a molecular marker; and
(b) further authenticating the petroleum product by the presence of the molecular marker.

12. The method of claim 11, wherein the molecular marker is phthalocyanine.

13. The method of claim 11, wherein the molecular marker is squaraine.

14. The method of claim 1, wherein the ion mobility spectroscopy technique comprises taking a sample of the petroleum product and introducing the sample into an ion mobility spectroscopy device.

15. The method of claim 13, wherein the sample is introduced into the ion mobility spectroscopy device as a vapor.

16. The method of claim 15, wherein the ion mobility spectroscopy device introduces the sample as a vapor by drawing the vapor from the headspace above a liquid sample.

17. The method of claim 15, wherein the vapors are ionized by a ionization source.

18. The method of claim 17, wherein the ionization source comprises a radioactive source that ionizes the vapor by the emission of low energy beta particles.

19. The method of claim 17, wherein the ionization source comprises as radioactive nickel source.

20. The method of claim 17, wherein the ionization source comprises nickel 63.

21. The method of claim 1, wherein the petroleum product is a fuel.

22. The method of claim 1, wherein the petroleum product is an oil.

23. The method of claim 1, wherein the petroleum product is a lubricant.

24. The method of claim 1, wherein the chemical marker has a boiling point between 100° C. and 250° C.

25. The method of claim 1, wherein the R group is at least three carbons long.

26. The method of claim 1, wherein the R' group is at least 3 carbons long.

* * * * *